United States Patent
Endo et al.

(10) Patent No.: US 8,079,709 B2
(45) Date of Patent: Dec. 20, 2011

(54) CORNEA SHAPE MEASUREMENT APPARATUS

(75) Inventors: Masakazu Endo, Aichi (JP); Masaaki Hanebuchi, Aichi (JP); Noriji Kawai, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 12/892,971

(22) Filed: Sep. 29, 2010

(65) Prior Publication Data

US 2011/0075098 A1    Mar. 31, 2011

(30) Foreign Application Priority Data

Sep. 30, 2009    (JP) ................. 2009-227949

(51) Int. Cl.
*A61B 3/10* (2006.01)
*A61B 3/00* (2006.01)
(52) U.S. Cl. .............. 351/212; 351/200; 351/205
(58) Field of Classification Search ............ 351/212, 351/200, 205, 211, 218, 221
See application file for complete search history.

(56) References Cited

U.S. PATENT DOCUMENTS

| | | | |
|---|---|---|---|
| 5,549,596 A * | 8/1996 | Latina | 606/4 |
| 6,755,528 B2 | 6/2004 | Isogai | |
| 2005/0107775 A1* | 5/2005 | Huang et al. | 606/5 |
| 2010/0060855 A1* | 3/2010 | Graether | 351/206 |
| 2010/0225014 A1* | 9/2010 | Bille | 264/1.37 |

* cited by examiner

*Primary Examiner* — Dawayne Pinkney
(74) *Attorney, Agent, or Firm* — Lowe Hauptman Ham & Berner LLP

(57) ABSTRACT

A cornea shape measurement apparatus outputs data useful for prescription as well as injection and installation of a TORIC-IOL. This apparatus includes: a projecting optical system projecting an index for measurement onto a cornea; an illuminating optical system illuminating an anterior segment on which a reference mark is placed; an imaging optical system capturing an anterior segment image containing the reference mark and an image of the index reflected from the cornea; an image processor overlaying an astigmatic axis mark indicating a direction of an astigmatic axis of the cornea, which is calculated based on the index image, on the anterior segment image; and a controller displaying the anterior segment image, which contains the astigmatic axis mark, on a display.

13 Claims, 4 Drawing Sheets

CORNEA SHAPE MEASUREMENT APPARATUS

CROSS-REFERENCE TO RELATED APPLICATION

This application is based on Japanese Patent Application No. 2009-227949 filed with the Japan Patent Office on Sep. 30, 2009, the entire content of which is hereby incorporated by reference.

BACKGROUND

1. Technical Field

The present invention relates to a cornea shape measurement apparatus for measuring a shape of a cornea of an examinee's eye.

2. Related Art

There has been known a cornea shape measurement apparatus for projecting an index for cornea shape measurement onto a cornea and capturing an image of the index reflected from the cornea to measure a shape of the cornea (e.g., refer to JP 2003-169778 A). A cornea shape obtained by such an apparatus has been used for determining a dioptric power of an intraocular lens (IOL), for example.

As an example of IOLs, recently, there has been proposed a TORIC-IOL for astigmatism correction. In a case of injecting a TORIC-IOL into a patient's eye (an examinee's eye), an operator (an examiner) previously measures an astigmatic axis of the patient's eye by use of a cornea shape measurement apparatus. Then, the operator places a first mark on the patient's eye in a direction of a horizontal axis by use of a dedicated member. Further, the operator places a second mark on the patient's eye in a direction of the astigmatic axis with respect to the first mark, and then injects the IOL into the patient's eye so as to align the second mark with an axis of the IOL.

However, when a posture of the patient varies at the time of measuring the cornea shape and at the time of placing the mark, the operator fails to properly place the mark on the patient's eye in the direction of the astigmatic axis. Consequently, there is a possibility of deviation of a position where the IOL is to be injected.

SUMMARY

An object of the present invention is to provide a cornea shape measurement apparatus capable of outputting data useful for prescription as well as injection and installation of a TORIC-IOL.

In order to accomplish this object, the present invention provides the following configurations.

That is, a cornea shape measurement apparatus includes: a projecting optical system that includes a first light source, and projects an index for cornea shape measurement onto a cornea of an examinee's eye; an illuminating optical system that includes a second visible light source which is different from the first light source, and illuminates an anterior segment of the eye, on which a reference mark for intraocular lens operations is placed, with visible light; an imaging optical system that includes an imaging device, and captures an anterior segment image containing the reference mark and an image of the index reflected from the cornea; a memory that stores therein the anterior segment image containing the reference mark and the index image, based on an output signal from the imaging device; a calculator that determines a direction of an astigmatic axis of the cornea, based on the index image in the memory; an image processor that overlays an astigmatic axis mark indicating the direction of the astigmatic axis on the anterior segment image in the memory, in accordance with a calculation result by the calculator; a display; and a controller that displays the anterior segment image, which is subjected to the image processing by the image processor so as to contain the astigmatic axis mark, on the display.

Preferably, the image processor overlays angle information for determining an angle between the reference mark and the direction of the astigmatic axis, on the anterior segment image.

Preferably, the illuminating optical system and the imaging optical system are each configured such that the imaging device receives light which is reflected from the anterior segment and has a wavelength characteristic of satisfying a complementary relation with a color of ink to be used for the reference mark.

Preferably, the illuminating optical system and the imaging optical system are each configured such that the imaging device receives light which is reflected from the anterior segment and has a wavelength characteristic that a center wavelength falls within a range from 500 nm to 600 nm.

Preferably, in a case where the color of ink to be used for the reference mark is one of blue and purple, the illuminating optical system and the imaging optical system are each configured such that the imaging device receives light which is reflected from the anterior segment and has a wavelength characteristic that a center wavelength falls within a green range.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Figure 1:
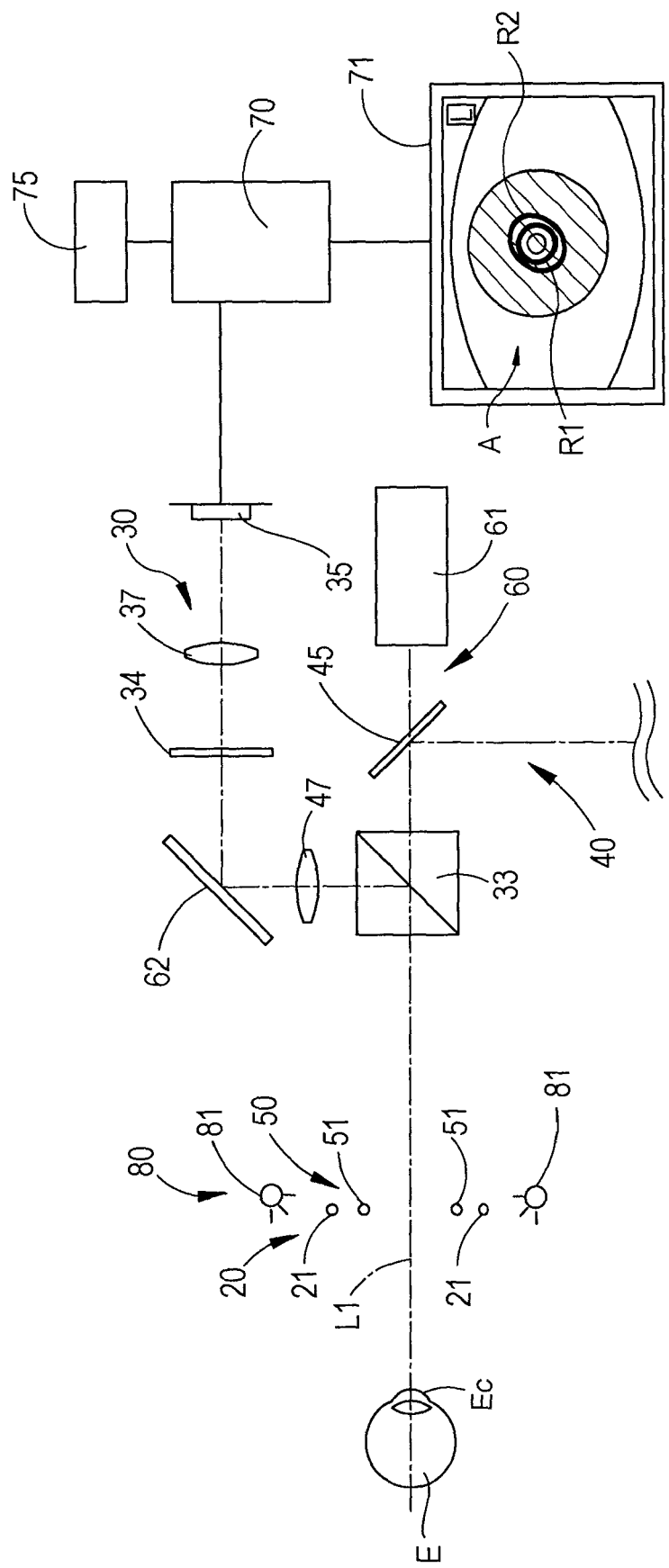
FIG. 1 illustrates a schematic configuration of an optical system and a control system in a cornea shape measurement apparatus according to one embodiment of the present invention.

Preferred embodiments of the present invention will be described below with reference to the accompanying drawings, in which like reference characters designate similar or identical parts throughout the several views thereof. FIG. 1 illustrates a schematic configuration of an optical system and a control system in a cornea shape measurement apparatus according to one embodiment of the present invention. In this apparatus, the optical system includes a cornea shape measuring index projecting optical system 20, an illuminating optical system 80, an alignment index projecting optical system 50, an imaging optical system 30, a measuring optical system 60 and a fixation index projecting optical system 40.

The projecting optical system 20 projects a ring index for cornea shape measurement onto a cornea Ec of an examinee's eye E. The illuminating optical system 80 illuminates an anterior segment of the examinee's eye E with visible light. The projecting optical system 50 projects a ring index for alignment status detection onto the cornea Ec. The imaging optical system 30 captures a front image of the anterior segment. The measuring optical system 60 measures an eye characteristic other than a cornea shape. The fixation index projecting optical system 40 is used for fixation of the examinee's eye E (i.e., fixes a line of sight). Herein, each optical system is incorporated in a housing (not illustrated). Moreover, the housing is shifted in a three-dimensional direction with respect to the examinee's eye E by a well-known shifting (moving) mechanism for alignment including an operating member (e.g., a joystick).

The projecting optical system 20 includes a ring-shaped light source 21 arranged about a measurement optical axis L1. The projecting optical system 20 is used for measuring a shape (e.g., a curvature, an astigmatic axis angle and the like in a direction of a strong principal meridian and a direction of a weak principal meridian) of the cornea Ec by projecting a ring index R2 onto the cornea Ec. Herein, examples of the light source 21 include an LED (Light Emitting Diode) that emits visible light or infrared light, and the like. Preferably, the light source of the projecting optical system 20 is at least three or more point light sources arranged on a single circumference about the optical axis L1. In other words, this light source may be an intermittent (discontinuous) ring-shaped light source. Furthermore, the projecting optical system 20 may be an optical system for projecting a plurality of ring indexes.

The illuminating optical system 80 includes a plurality (four in this embodiment) of green light sources (e.g., LEDs that emit green light) 81 arranged outside the light source 21 about the optical axis L1. The light source 81 illuminates the anterior segment with green light, and is used for capturing an anterior segment image (see FIG. 2B) containing a blue or purple mark M.

The mark M is placed with ink on a white portion of the examinee's eye E in order to carry out operations for injection of an intraocular lens for astigmatism correction (a TORIC-IOL). This mark M corresponds to a first mark (a reference mark) which is placed on the examinee's eye E in a direction of a horizontal axis. As the light source 81, for example, there is used a green light source that emits green light which has a center wavelength of 525 nm and falls within a wavelength range from 500 nm to 550 nm. However, the light source 81 is not limited to such a green light source. For example, the light source 81 may be a white light source. In such a case, a filter having a characteristic of allowing only green light to transmit therethrough may be provided forward the light source 81.

The projecting optical system 50 includes an infrared light source 51 (e.g., an LED that emits infrared light having a center wavelength of 970 nm) arranged inside the light source 21 about the optical axis L1. The light source 51 is used for projecting an alignment index onto the cornea Ec. The alignment index projected on the cornea Ec is used for alignment (positioning) of the apparatus with respect to the examinee's eye E. In this embodiment, the projecting optical system 50 is an optical system for projecting a ring index R1 onto the cornea Ec. Moreover, the projecting optical system 50 (the light source 51) also serves as an illuminating optical system (a light source) for illuminating the anterior segment with infrared light in an oblique direction.

The imaging optical system 30 is used for capturing the front image of the anterior segment. The imaging optical system 30 includes a dichroic mirror (a beam splitter) 33, an objective lens 47, a total reflection mirror 62, a filter 34, an imaging lens 37 and a two-dimensional imaging device (a light receiving device) 35.

Each of the reflected light from the anterior segment based on the light from the projecting optical system 20 (the light source 21), the reflected light from the anterior segment based on the light from the illuminating optical system 80 (the light source 81) and the reflected light from the anterior segment based on the light from the projecting optical system 50 (the light source 51) is reflected by the dichroic mirror 33, transmits through the objective lens 47, is reflected by the total reflection mirror 62, and transmits through the filter 34. Based on each reflected light, an image is formed on the imaging device 35 through the imaging lens 37. In other words, the imaging device 35 has a sensitivity range from visible light to infrared light.

The imaging optical system 30 captures an image of the anterior segment by use of the light emitted from the light source 21. Thus, the imaging optical system 30 can capture an anterior segment image A that contains the ring index R2 (i.e., a cornea reflection image) formed on the cornea Ec. In the case where the mark M is placed on the examinee's eye E, moreover, the imaging optical system 30 captures an image of the anterior segment by use of the light emitted from the light source 81. Thus, the imaging optical system 30 can capture an anterior segment image A that contains the mark M.

The filter 34 is used for allowing the visible light or infrared light from the light source 21, the green light from the light source 81, and the infrared light from the light source 51 to transmit therethrough, but blocking light other than the light mentioned above.

The measuring optical system 60 includes a measuring optical unit 61 and a dichroic mirror 45. The measuring optical unit 61 has such a configuration as to project infrared measurement light onto the examinee's eye E and receive the reflected light from the examinee's eye E. The dichroic mirror 45 has a characteristic of allowing infrared light to transmit therethrough, but reflecting visible light.

Examples of the measuring optical system 60 may include an axial length measuring optical system (e.g., a center wavelength of a measurement light source is 830 nm) for measuring an axial length by receiving interference light of infrared measurement light, which is projected onto and then reflected from a fundus, with infrared reference light, an eye refractive power measuring optical system (e.g., a center wavelength of a measurement light source is 870 nm) for measuring an eye refractive power by receiving infrared measurement light which is projected onto and then reflected from a fundus, and the like.

The projecting optical system 40 that includes a visible light source is arranged in a direction of reflection by the dichroic mirror 45.

The following description is given about the control system. A calculation control part 70 performs various operations, e.g., controls the entire apparatus, and calculates a result of measurement. The light source 21, the light source 81, the light source 51, the imaging device 35, the measuring optical unit 61, the fixation index projecting optical system 40, a monitor (a display) 71, a memory 75 and the like are connected to the calculation control part 70. An output signal (a signal of an anterior segment image) from the imaging device 35 is input to the calculation control part 70, and then is subjected to image processing. An image obtained by this processing is displayed as an anterior segment image on the monitor 71. Moreover, the calculation control part 70 detects an alignment status of the apparatus with respect to the examinee's eye E, based on a result of image processing for an output signal (a signal of an alignment index) from the imaging device 35.

Figure 2A:
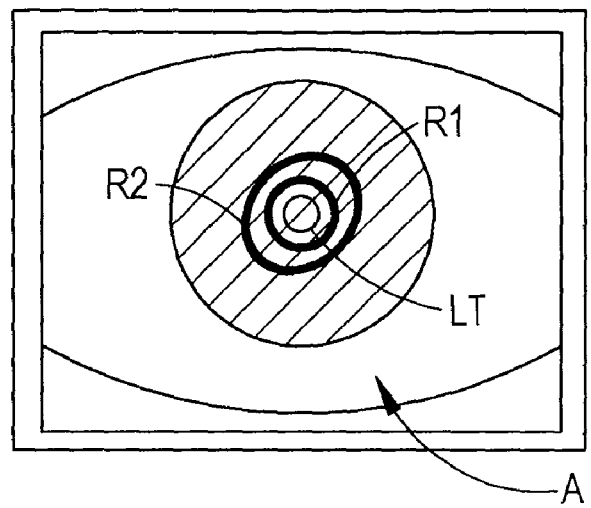
FIGS. 2A and 2B each illustrate an observation screen on which an anterior segment image is displayed.
Figure 2B:
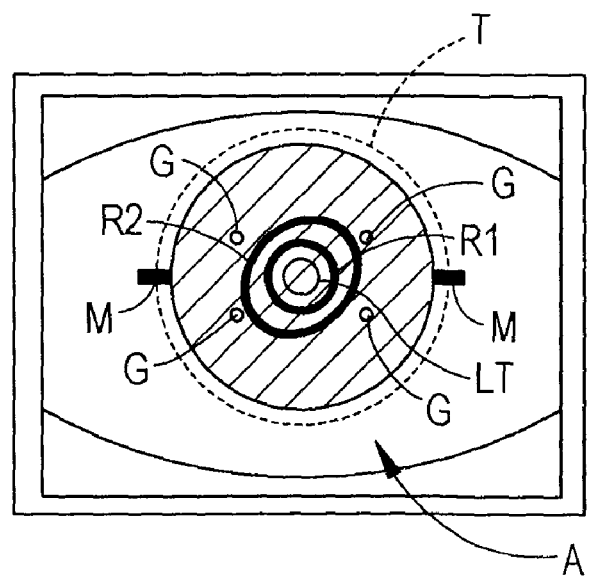

The following description is given about operations of the apparatus configured as described above. FIGS. 2A and 2B each illustrate an observation screen on which an anterior segment image captured by the imaging device 35 is displayed. Upon alignment, the light source 21 and the light source 51 each emit light. As illustrated in FIG. 2A, the examiner conducts alignment of the apparatus in an up-to-down direction and a left-to-right direction with respect to the examinee's eye E such that an electrically displayed reticle LT is aligned concentrically with the ring index R1 from the light source 51. Moreover, the examiner conducts alignment of the apparatus in a forward-to-backward direction (a working distance direction) with respect to the examinee's eye E such that the ring index R1 is brought into focus (i.e., the ring index R1 is displayed clearly).

Subsequent to the alignment described above, a predetermined trigger signal is generated. Then, the calculation control part 70 causes the light source 81 to emit light, and causes the imaging device 35 to capture an anterior segment image. Based on an output signal from the imaging device 35 (i.e., a signal of the anterior segment image), the calculation control part 70 acquires, as a still image, an anterior segment image that contains the ring index R1, the ring index R2 and the mark M, and stores the still image in the memory 75 (see FIG. 2B). In FIG. 2B, four bright spots G each represent a cornea reflection image based on the light from the light source 81. Herein, the operation of measuring the cornea shape and the operation of taking the image of the mark M are conducted simultaneously. However, these operations may be conducted at different timings, respectively.

Next, the calculation control part 70 determines the cornea shape, based on the ring index R2 in the anterior segment image stored in the memory 75, and stores the result of determination in the memory 75. In a case of a corneal astigmatism eye, such a ring index R2 has an oval shape. With regard to this ring index R2, therefore, the calculation control part 70 detects a direction of a longer diameter and a direction of a shorter diameter to determine an angle of an astigmatic axis. Herein, the cornea shape may be determined based on the ring index R1 in addition to the ring index R2.

Figure 3:
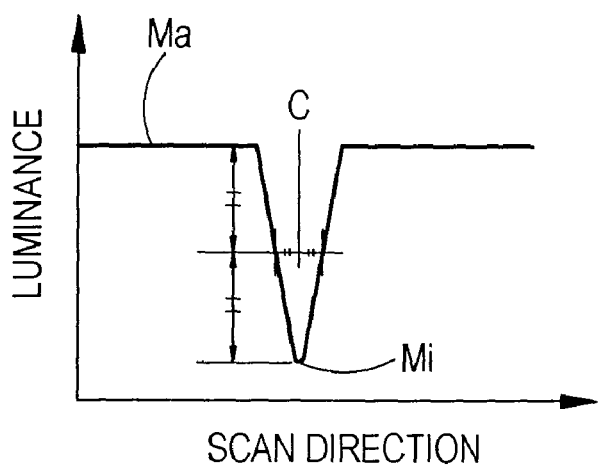
FIG. 3 illustrates luminance distribution in the anterior segment image.

Moreover, the calculation control part 70 detects a position of the mark M in the anterior segment image stored in the memory 75, and stores the result of detection in the memory 75. More specifically, the calculation control part 70 detects a position of a ring-shaped boundary between an iris and a white portion in an eye, based on image processing, and then determines luminance distribution at a position located outward by a predetermined amount with respect to the boundary (see a dotted line T in FIG. 2B). As illustrated in FIG. 3, then, the calculation control part 70 detects a portion, where a luminance level is lowered maximumly with respect to a luminance level Ma, in the white portion of the eye, (a luminance level Mi) from the luminance distribution, and specifies the position C of the mark M, based on the result of detection. Thus, the calculation control part 70 detects positions of two marks M which are symmetrical with each other with respect to a center of a pupil (or a center of the cornea).

Figure 4:
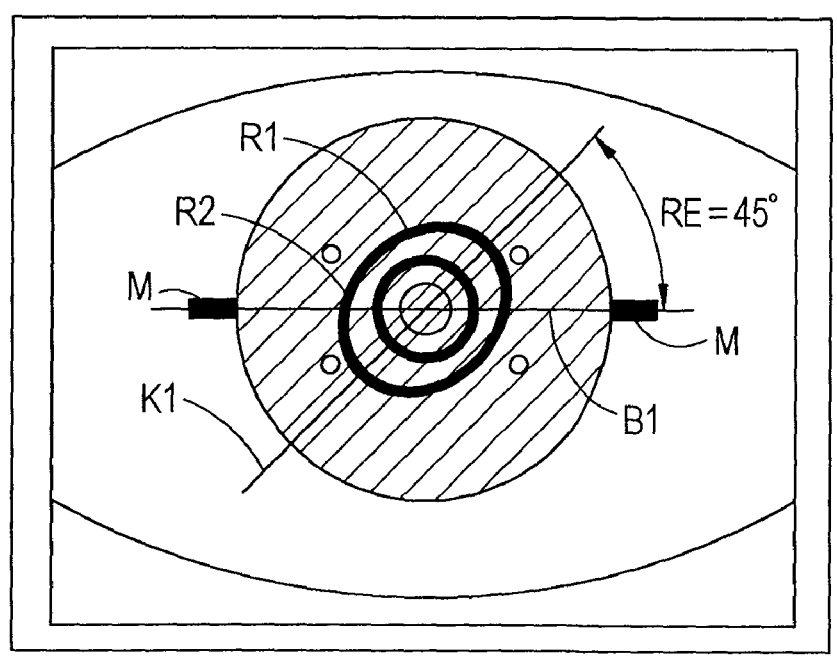
FIG. 4 illustrates anterior segment image data for use in injection of an intraocular lens for astigmatism correction.

FIG. 4 illustrates anterior segment image data for use in injection of the intraocular lens for astigmatism correction into the examinee's eye E. The calculation control part 70 prepares the anterior segment image data illustrated in FIG. 4, based on the results of measurement and the results of detection, and then displays the data on the monitor 71.

In FIG. 4, a line K1 and a line B1 are each displayed electrically in such a manner that the anterior segment image stored in the memory 75 is subjected to image processing. The line K1 is a mark indicating the direction of the astigmatic axis of the cornea with respect to the mark M. The line B1 is a mark indicating a reference axis for conducting marking in the direction of the astigmatic axis, and corresponds to the mark M. That is, the line B1 passes the two marks M.

Herein, the calculation control part 70 determines an angle of the line K1, based on the angle of the astigmatic axis calculated as described above. Then, the calculation control part 70 displays the line K1 combinedly on the anterior segment image such that the line K1 passes the center of the ring index R2 in the anterior segment image. Based on the positions of the two marks M detected as described above, moreover, the calculation control part 70 displays the line B1, which connects between the two marks M, combinedly on the anterior segment image.

Based on the result of calculation of the angle of the astigmatic axis and the result of detection of the mark M, further, the calculation control part 70 calculates an angle between the mark M (the line B1) and the direction of the astigmatic axis (the line K1). The result of calculation may be displayed combinedly as an angle RE on the anterior segment image (see FIG. 4).

The calculation control part 70 stores the anterior segment image data prepared by the image processing in the memory 75. The calculation control part 70 causes the monitor 71 to display the anterior segment image data. In addition, the calculation control part 70 causes a printer to output the data as printed matter. The anterior segment image data (the output data) illustrated in FIG. 4 is used for placing a second mark (an astigmatic axis mark) on a position of the eye corresponding to the astigmatic axis of the cornea.

Based on the anterior segment image data illustrated in FIG. 4, the operator can ascertain the direction of the astigmatic axis relative to the first mark M indicating the reference axis. Therefore, the operator can place the second mark corresponding to the direction of the astigmatic axis on an appropriate position on the cornea. Thus, the operator can easily inject the TORIC-IOL into an appropriate position of the patient's eye.

According to the configuration described above, the anterior segment image containing the mark M is captured using the light from the green light source 81, so that a contrast between the anterior segment image (e.g., the anterior segment image illustrated in FIG. 2A) and the mark M becomes clear in the anterior segment image data illustrated in FIG. 4. Thus, the operator can visually identify the mark M with ease. The reason therefor is as follows. That is, the mark M is placed with blue ink or purple ink in general, and the green light which is emitted from the light source 81 is not reflected because of the ink since the green light does not interfere with blue light or purple light in view of the principle of three primary colors (red, blue, green). Thus, a contrast between the mark M and the white portion of the eye becomes more remarkable. Herein, purple is a mixed color of red with blue. The present inventors have conducted experiments using different colors other than green. As the results of experiments, the present inventors have found out that in the case of using blue light, the blue mark M becomes poor in visibility whereas in the case of using red light, the purple mark M becomes poor in visibility.

In the foregoing description, the illuminating optical system 80 illuminates the anterior segment with the green light.

However, the configuration of the illuminating optical system 80 is not limited to that described above. For example, the illuminating optical system 80 may be configured to illuminate the anterior segment with light which falls within such a wavelength range as to hardly interfere with the color of ink to be used for the mark M (e.g., light having a center wavelength in a range from 500 nm to 600 nm). In other words, the illuminating optical system 80 may illuminate the anterior segment with light having a wavelength characteristic of satisfying a complementary relation with the color of ink to be used for the mark M. Preferably, the light source to be used herein is excellent in monochromaticity.

In the foregoing embodiment, the illuminating optical system 80 adopts one type light source in order to take an image of the mark M. However, the configuration of the illuminating optical system 80 is not limited to that described above. For example, the illuminating optical system 80 may include at least two type light sources which are different in center wavelength from each other, and switches between the light sources in accordance with the color of the mark M in order to prevent light emitted from the light source from interfering with the color of the mark M.

Further, the configuration of the illuminating optical system 80 and the configuration of the imaging optical system 30 are not limited to those described above as long as the imaging device 35 receives light which is reflected from the anterior segment and has a wavelength characteristic of satisfying a complementary relation with the color of the mark M. For example, the illuminating optical system 80 may include a white light source. Further, a filter that allows green light and infrared light to transmit therethrough, but absorbs light other than the green light and infrared light may be arranged on an optical path of the imaging optical system 30.

In the foregoing description, moreover, the result of detection (i.e., the angle RE between the mark M (the line B1) and the direction of the astigmatic axis (the line K1)) is output. However, the present invention is not limited to this configuration as long as angle information for determining the angle between the mark M and the direction of the astigmatic axis is displayed together with the anterior segment image. For example, an angle scale (e.g., a protractor) for determining an angle between the mark M (the line B1) and the line K1 may be displayed combinedly with the anterior segment image. In such a case, preferably, scales are drawn with the position of the mark M being defined as 0 degree.

Moreover, the configuration of the calculation control part 70 is not limited to that described above. For example, the calculation control part 70 may rotate the line K1 displayed on the screen of the monitor 71, based on an operating signal from a predetermined switch which is actuated manually by the examiner. In such a case, the calculation control part 70 may measure a rotation angle of the line K1 which matches with the mark M. Alternatively, the calculation control part 70 may rotate the line B1 displayed on the screen of the monitor 71 and may measure a rotation angle of the line B1.

Figure 5:
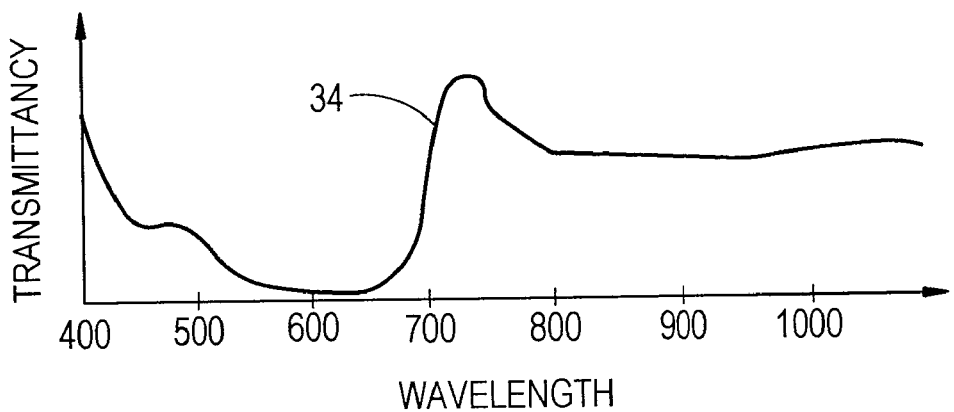
FIG. 5 illustrates an example of a wavelength characteristic of a filter arranged in an imaging optical system.

FIG. 5 illustrates an example of a wavelength characteristic of a filter 34. The filter 34 is subjected to coating to allow the green light (500 nm to 550 nm) from the light source 81 and the infrared light from the light sources 21 and 51 to transmit therethrough.

Herein, the green light range is set to be considerably smaller in transmittancy than the infrared light range in order to deal with variations in sensitivity characteristics among imaging devices 35 which are usable herein and to intercept (cut) visible disturbance light (e.g., light from a fluorescent lamp). Preferably, an output from, i.e., a luminance of the light source 81 is large since the transmittancy in the green light range is small.

Figure 6:
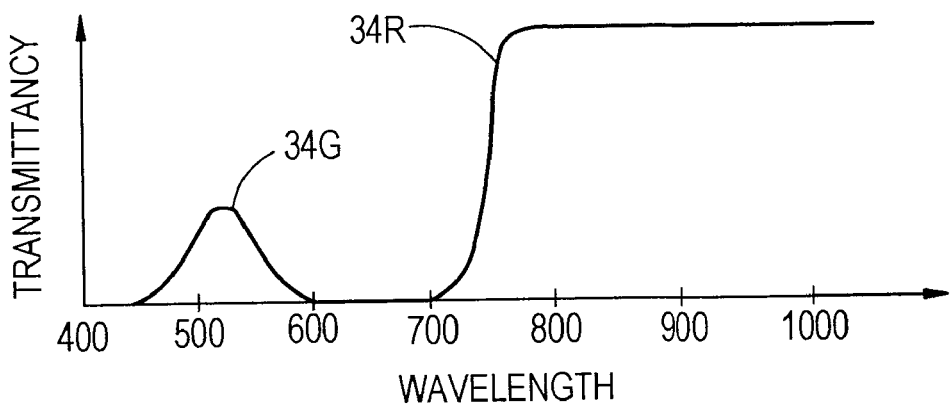
FIG. 6 illustrates a wavelength characteristic of a filter for taking an image of a reference mark and a wavelength characteristic of a filter for taking an image of an index for cornea shape measurement and an image of an alignment index.

In place of the filter 34, a filter 34G for taking an image of the mark M and a filter 34R for taking images of the ring indexes R1 and R2 may be arranged in a switchable manner (see FIG. 6).

While the invention has been illustrated and described in detail, the foregoing description is in all aspects illustrative and not restrictive. It is therefore understood that numerous modifications and variations can be devised without departing from the spirit and scope of the invention.

What is claimed is:

1. A cornea shape measurement apparatus, comprising:
a projecting optical system that includes a first light source for projecting an index for cornea shape measurement onto a cornea of an examinee's eye;
an illuminating optical system that includes a second visible light source, which is different from the first light source, for illuminating, with visible light, an anterior segment of the eye, on which a reference mark for injecting a toric intraocular lens for astigmatism correction (TORIC-IOL) is placed;
an imaging optical system that includes a two-dimensional imaging device for capturing, at different timings,
  (i) an index image of the index reflected from the cornea, and
  (ii) an anterior segment front image for the TORIC-IOL, wherein the anterior segment front image the TORIC-IOL contains the reference mark but does not contain the index;
a controller for
  (a) turning on the first light source to cause the two-dimensional imaging device to capture the index image, based on light which is emitted from the first light source and then reflected from the cornea, and
  (b) turning on the second visible light source on at a different timing from the first light source to cause the two-dimensional imaging device to capture the anterior segment front image for the TORIC-IOL, based on the visible light which is emitted from the second visible light source and then reflected from the anterior segment of the eye;
a memory for storing therein the index image and the anterior segment front image for the TORIC-IOL, based on an output signal from the two-dimensional imaging device;
a calculator for determining a direction of an astigmatic axis of the cornea, based on the index image stored in the memory;
an image processor for overlaying an astigmatic axis mark indicating the direction of the astigmatic axis on the anterior segment front image for the TORIC-IOL stored in the memory, in accordance with a calculation result by the calculator; and
an output appliance for outputting the anterior segment front image for the TORIC-IOL that contains the astigmatic axis mark overlaid by the image processor.

2. The cornea shape measurement apparatus according to claim 1, wherein
the calculator is further arranged for calculating angle information about an angle between the direction of the astigmatic axis and the reference mark, based on the calculation result of the astigmatic axis and positional information of the reference mark, and the image processor is further arranged for overlying the calculated angle information on the anterior segment front image for the TORIC-IOL.

3. The cornea shape measurement apparatus according to claim 1, wherein
the illuminating optical system and the imaging optical system are each configured such that the two-dimensional imaging device receives light which is reflected from the anterior segment and has a wavelength characteristic satisfying a complementary relation with a color of ink to be used for the reference mark.

4. The cornea shape measurement apparatus according to claim 3, wherein
the illuminating optical system and the imaging optical system are each configured such that the two-dimensional imaging device receives light which is reflected from the anterior segment and has a wavelength characteristic that a center wavelength falls within a range from 500 nm to 600 nm.

5. The cornea shape measurement apparatus according to claim 4, wherein
in a case where the color of ink to be used for the reference mark is one of blue and purple, the illuminating optical system and the imaging optical system are each configured such that the two-dimensional imaging device receives light which is reflected from the anterior segment and has a wavelength characteristic that a center wavelength falls within a green range.

6. The cornea shape measurement apparatus according to claim 2, wherein
the calculator is further arranged for processing the anterior segment front image for the TORIC-IOL to detect the positional information of the reference mark, and calculating the angle information about the angle between the direction of the astigmatic axis and the reference mark, based on the calculation result of the astigmatic axis and the detected positional information of the reference mark.

7. The cornea shape measurement apparatus according to claim 2, further comprising:
an operating unit manually actuable by an examiner, wherein
the output appliance is a display for displaying a line rotating based on an operating signal from the operating unit, and
the calculator is further arranged for calculating a rotation angle of the line at a position between the astigmatic axis mark and the reference mark to calculate the angle information about the angle between the direction of the astigmatic axis and the reference mark.

8. The cornea shape measurement apparatus according to claim 3, wherein
the imaging optical system includes a filter, that is installed on an optical path for capturing the anterior segment front image for the TORIC-IOL containing the reference mark, for transmitting light, which is reflected from the anterior segment and has a wavelength characteristic satisfying a complementary relation with a color of ink to be used for the reference mark.

9. The cornea shape measurement apparatus according to claim 8, wherein
the second visible light source is a green light source, and
the filter transmits green light reflected from the anterior segment.

10. The cornea shape measurement apparatus according to claim 1, wherein
the first light source is an infrared light source.

11. The cornea shape measurement apparatus according to claim 1, wherein
the first light source includes a plurality of point light sources.

12. The cornea shape measurement apparatus according to claim 1, wherein
the output appliance is a display.

13. The cornea shape measurement apparatus according to claim 1, wherein
the output appliance is a printer.

* * * * *